United States Patent [19]
Wainwright et al.

[11] Patent Number: 5,876,918
[45] Date of Patent: *Mar. 2, 1999

[54] ALIGNED FIBER DIAGNOSTIC CHROMATOGRAPHY WITH POSITIVE AND NEGATIVE CONTROLS

[75] Inventors: Norman Wainwright; Steven H. Boyd, both of Falmouth, Mass.

[73] Assignee: Hydros, Inc., Falmouth, Mass.

[*] Notice: This patent issued on a continued prosecution application filed under 37 CFR 1.53(d), and is subject to the twenty year patent term provisions of 35 U.S.C. 154(a)(2).

[21] Appl. No.: 513,763

[22] PCT Filed: Mar. 7, 1994

[86] PCT No.: PCT/US94/02411

§ 371 Date: Aug. 29, 1995

§ 102(e) Date: Aug. 29, 1995

[87] PCT Pub. No.: WO95/04037

PCT Pub. Date: Feb. 9, 1995

Related U.S. Application Data

[63] Continuation-in-part of Ser. No. 27,813, Mar. 8, 1993, abandoned.

[51] Int. Cl.⁶ ............... C12Q 1/00; G01N 33/543; B01L 3/02
[52] U.S. Cl. ............... 435/4; 435/6; 435/7.1; 435/287.2; 435/287.9; 436/501; 422/100; 422/101
[58] Field of Search ............... 435/4, 6, 7.1, 287.2, 435/287.8, 287.9; 436/501; 422/100, 101

[56] References Cited

U.S. PATENT DOCUMENTS 3,095,343 6/1963 Berger .
3,111,702 11/1963 Berger .
4,541,987 9/1985 Guadagno ............... 422/56
4,657,742 4/1987 Beaver ............... 422/240
4,775,619 10/1988 Urdea ............... 435/6
4,806,313 2/1989 Ebersole et al. ............... 422/61
4,933,291 6/1990 Daiss et al. ............... 436/45
5,006,462 4/1991 Gattaz ............... 435/7.4
5,053,066 10/1991 Hassenboehler ............... 55/521
5,139,680 8/1992 Tarnopolsky ............... 210/656
5,171,537 12/1992 Wainwright et al. ............... 422/100
5,200,321 4/1993 Kidwell ............... 435/7.9
5,268,146 12/1993 Lawrence et al. ............... 422/57
5,385,707 1/1995 Miltenyi et al. ............... 422/69
5,695,928 12/1997 Stewart ............... 435/5

FOREIGN PATENT DOCUMENTS

88/09201 of 1988 WIPO .
92/21968 of 1992 WIPO .
93/00163 of 1993 WIPO .

OTHER PUBLICATIONS

Czok et al., *J. Chromatog.* 506, 303–317 (1990).

Nucleic Acids Research, vol. 13, No. 15, 1985, Delius, et al. pp. 5457–5469.

*Primary Examiner*—Kenneth R. Horlick
*Attorney, Agent, or Firm*—Nields, Lemack & Dingman

[57] ABSTRACT

A preactivated chromatography tip having covalent coupling functionality within a hydrodynamically designed micropipette tip assembly. The preactivated micro-channeled element provides high fluid directionality and throughput with minimum backpressure. A fibrous capture element is designed to optimize surface area to volume ratio, chemical resistance, a specific directional flow pattern, low non-specific binding of ligands, small sample volume, speed and low background.

8 Claims, 3 Drawing Sheets

ALIGNED FIBER DIAGNOSTIC CHROMATOGRAPHY WITH POSITIVE AND NEGATIVE CONTROLS

This application is a continuation-in-part of U.S. patent application Ser. No. 08/027,813 filed Mar. 8, 1993, abandoned.

BACKGROUND OF THE INVENTION

From the beginning of the science of chromatography, fibers have been employed extensively. Fibers were used as surfaces that were selectively adherent to compounds to be separated. Complex mixtures of molecules would bind to the fibers and be selectively removed by solvent systems. Cellulose is a common fiber comprised of linear polymer of beta 1,4-linked D-glucose, with beat 1,6 crosslinks. Paper chromatography is the classic example, initially used to separate colored molecules as an organic solvent wicked up the paper. The use of chemically derivatized paper fibers, such as cellulose acetate, quickly followed. A powdered form of such derivatized cellulose acetate became the basis of ion exchange and affinity column chromatography in which glass columns were packed with a slurry of cellulose fibers.

While these cellulosic columns were effective in increasing the surface area used to separate compounds, they were sorely deficient in resolving very similar molecules. The use of high flow rates to speed separations, created high back pressure, uneven packing and channelling. These deficiencies were due to the limitations of the physical structure of the fibers themselves. The particles of cellulose were of random length and their orientation in the column was totally random. This resulted in a column having a non-uniform pore size and areas of the column that could form a microcrystalline packing structure, thereby obstructing flow.

One particular application for diagnostic chromatography is DNA strand separation. Heretofore DNA strand separation techniques have been utilized in performing DNA sequence analysis of amplified DNA fragments. Typically, streptavidin, a protein having a very high affinity for binding biotin, is coated (immobilized) onto a solid support, such as for example magnetic microspheres or microtiter plates. When magnetic microspheres are used, the disadvantage is that optimal capture of the biotinylated DNA requires constant mixing of the sample with the streptavidin coated microspheres. Moreover, magnetic collection of the coated microspheres often is incomplete, especially when viscous samples are employed. When microtiter plates are utilized, cross contamination often occurs, and such plates have low binding capacity.

Still another method which utilizes a solid support for the reactive coating is disclosed in our U.S. Pat. No. 5,171,537. This patent teaches the use of a pipette tip containing a glass bead, or the like, which is mounted for limited movement in the tip intermediate its ends. The bead is coated with a receptor, such as a single ligand having an affinity for a specific target molecule in a fluid sample that is to be drawn into the tip by an associated pipetting instrument. While this type of tip is particularly suitable for use in a variety of different test procedures, the quantity of target molecule which can be captured by the receptor element is limited by the surface area of the spherical support.

It is therefore an object of the present invention to provide a preactivated chromatography tip having covalent coupling functionality within a hydrodynamically designed micropipette tip assembly.

It is a further object of the present invention to provide a preactivated chromatography tip through which flow is not restricted and rapid flow rates are possible.

It is a still further object of the present invention to provide a preactivated chromatography tip which enables the detection of proteins including proteases, nucleases, antibodies, antigens and haptens.

These and other objects of the invention will become apparent from the specification and the appended claims.

SUMMARY OF THE INVENTION

The problems of the prior art have been overcome by the present invention, which provides a preactivated chromatography tip having covalent coupling functionality within a hydrodynamically designed micropipette tip assembly. The preactivated micro-channeled element provides high fluid directionality and throughput with minimum backpressure. A fibrous capture element is designed to optimize surface area to volume ratio, chemical resistance, a specific directional flow pattern, low non-specific binding of ligands, small sample volume, speed and low background.

The accuracy and speed which diagnostic assays can be performed are enhanced by using a micropipette tip containing a porous reactive element through which a liquid sample is adapted to be aspirated and expelled such as by an associated pipetting instrument or by unidirectional dual port flow through in a column mode. The porous element presents a myriad of surfaces to the sample passing therethrough. These surfaces are coated with a receptor or ligand designed to capture predetermined molecules from the sample passing through the element. Because of the large, reactive surface area thus presented to a sample, the capture rate of the reactive element is 100 to 1000 fold grater than that achieved by receptors which are coated onto solid supports, such as microtiter plates, magnetic microspheres, and the beads disclosed in our above-noted U.S. patent.

The preactivated device includes one or more solid micro-channeled elements having porous capillary cell cavities which run longitudinally and flexibly direct fluids without difusional transport down fiber conduits. The elements are designed to optimally expose ligand receptors and minimize crossflow and adsorption of antigens or ligand detectors. The accuracy and speed with which ligand detection can be performed in the field or non-laboratory environment is enhanced using the present portable, self-contained device.

DETAILED DESCRIPTION OF THE INVENTION

Figure 1:
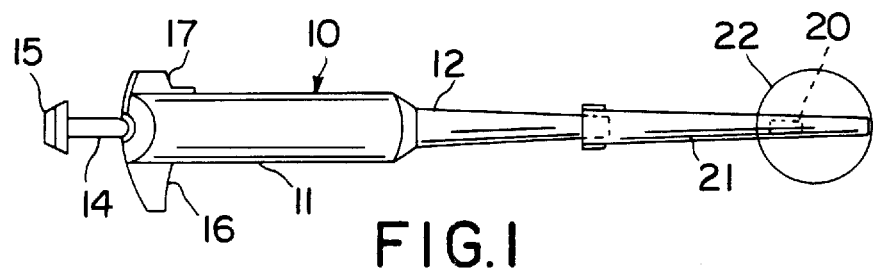
FIG. 1 is a side elevational view of a conventional aspirator-type pipettor or pipetting instrument having thereon a removable pipette tip made according to one embodiment of the present invention.
Figure 2:
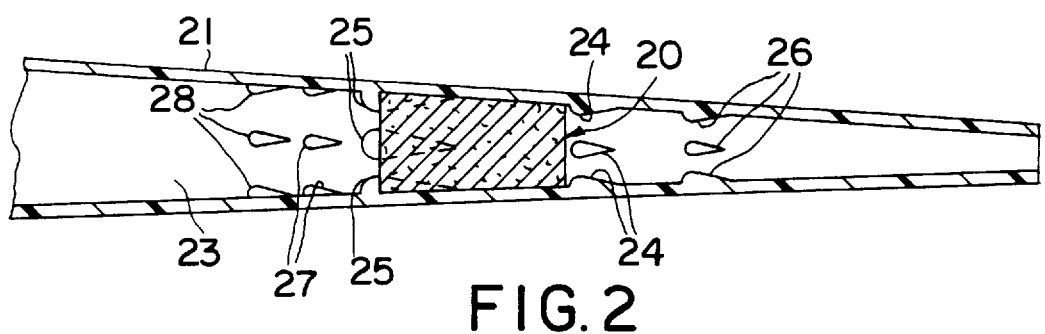
FIG. 2 is an enlarged, fragmentary, axial section view taken through that portion of the tip which is enclosed within the circle shown in FIG. 1.

Referring now to the drawings by numerals of reference, and first to FIGS. 1 and 2, numeral 10 denotes generally an aspirator-type pipetting instrument having a tubular body section 11, an integral, tapered nozzle section 12, and an operating rod or a shaft 14, which projects slidably out of the end of section 11 remote from its nozzle section 12. A head 15 on the outer end of rod 14 is adapted to be manipulated in the usual manner to reciprocate rod 14, and hence the attached piston (not illustrated) which is mounted in the body section 11 for reciprocation during the operation of the instrument. Conventional finger grips 16 and 17 project from opposite sides of section 11 for use in holding and manipulating the instrument.

Removably secured over the open end of the nozzle section 12 is a disposable pipette tip 21 a portion of which (the portion enclosed in the circle 22 in FIG. 1) has been enlarged and shown in cross-section in FIG. 2. Suitable materials for the pipette tip 21 include nylon, polycarbonate, TEFLON, polyvinyl fluoride, polystyrene, polypropylene, acrylic and polysulphone; the important limitation being the minimization of non-specific binding on the tip. Lodged in the bore 23 of tip 21 between two axially spaced sets or arrays of projections 24 and 25 is a truncated conical receptor element 20. Projections 24 and 25 are integral with and project radially inwardly from the inner peripheral surface of the tip 21 at equiangularly spaced points around its longitudinal axis. Additional arrays of projections are denoted at 26, 27 and 28; and all such projections are generally tear-shaped in configuration, and have their pointed ends facing the smaller end of the tip 21. Projections 24 through 28 are similar to those disclosed in our above-noted U.S. Pat. No. 5,171,537 (the disclosure of which is hereby incorporated by reference), and perform substantially the same function, namely, securing the receptor element 20 in the tip, and enhancing turbulence in the tip when a fluid sample is drawn into or discharged from the tip.

Figure 6:
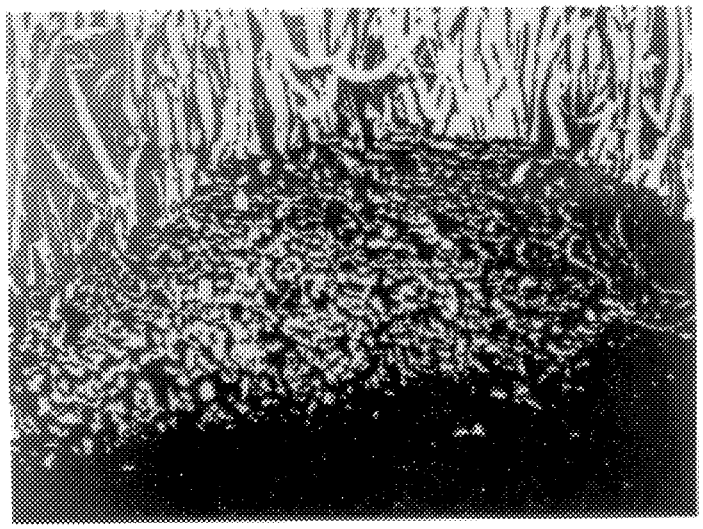
FIG. 6 is a scanning electron micrograph of a cross-section of the fibrous element in accordance with the present invention at a magnification of 40×.
Figure 7:
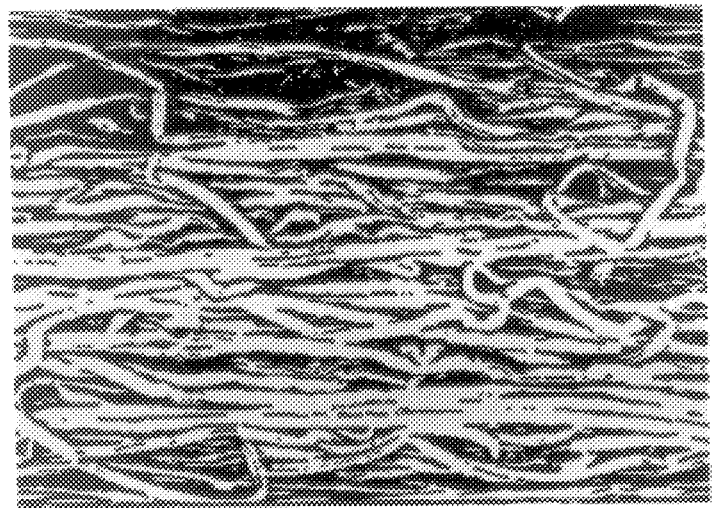
FIG. 7 is a scanning electron micrograph of a longitudinal view of the fibrous element in accordance with the present invention at a magnification of 40×.
Figure 8:
FIG. 8 is a scanning electron micrograph of a longitudinal view of the fibrous element in accordance with the present invention at a magnification of 300×.

Unlike the above-noted solid supports which were previously utilized to provide a substrate for the receptor coating, the reactive element 20 (FIG. 2) is made from a porous material, preferably non-biaxially oriented fibers made from cellulose acetate or the like, such as those described in U.S. Pat. Nos. 3,095,343 and 3,111,702, the disclosures of which are herein incorporated by reference. The fibers are arranged so as to be continuous from one end of the element to the other, thereby preventing microcrystalline packing, and are longitudinally oriented in the direction of fluid flow (FIGS. 6–8). In this way, the flow of liquid sample through the fibers follows a substantially parallel linear path, which has the effect of increasing local turbulence at the sample-ligand interface and increases ligand and analyte contact, thereby increasing the kinetics of binding, with a much greater binding capacity than a standard microtiter plate. This is best seen in FIG. 8. The quantity of bound molecules can amount to several micrograms, accumulating enough material to collect for further biochemical manipulation. Preferably each fiber bundle element has a diameter of from about 2 mm to about 8 mm. The length of each element should be greater than 1.5 times its width, in order to prevent the element from turning sideways in the tip. FIG. 6 illustrates the loose packing of fibers and open nature of space between fibers for unobstructed flow through the element. FIG. 7 illustrates the alignment of fibers, although some fibers became misaligned by cutting for display and photography. FIG. 8 illustrates the tortuous path the liquid must take during flow through the element.

The fibrous reactive element can be adapted to covalently capture amine ($-NH_2$), carboxyl ($-COOH$), sulhydral ($-SH$) and thiol bearing molecules. The batch preparation of such elements requires a sequential series of covalent activation steps involving a specific linker molecule and covalent coupling sequence. A step-wise plurality of reagents are required to obtain covalent non-ionic or non-hydrophobic coupling. The use of covalent coupling allows spacer arms or molecule extensions that connect two reactive molecular ends, thereby reducing steric hinderance and enhancing stability of the binding groups. Commonly used hetero- and homo-bifunctional crosslinkers include NHS esters, maleimides, pyridyl disulfides, active halogens, aldehydes, etc. Typical coupling reactions include antibodies, enzymes, haptens, antigens, toxins, vitamins, nucleases, nucleotides, endotoxins, etc. A protein captured on the element by binding to an immobilized antibody may be eluted and subjected to: analysis by gel electrophoresis, amino acid composition, sequencing, or may be included as a purified standard in a pilot assay procedure. If the bound material is nucleic acid (RNA, DNA), recombinant DNA cloning procedures or nucleotide sequencing may be performed. The rigid nature of the fibrous element holds the fiber, and the associated spaced between fibers, as a stable structure.

In an alternative embodiment of the present invention, the high binding capacity per volume ratio of the porous element allows small amounts of the porous element to be stacked in a multi-layered format. Each layer may be pre-coated with the appropriate molecules so they either capture multiple molecules for simultaneous assay, or are pre-bound with the appropriate molecules for positive and negative controls. The containment of the multiple layers within the single tip allows for concurrent measurement of unknowns and controls, minimizing assay error, especially of single measurements. Quality assurance of results, particularly with assays performed in non-laboratory settings, is augmented.

Yet another application of the aligned fiber diagnostics chromatography is the detection of nuclease contamination in reagents and samples used in molecular biology and clinical nucleic acid diagnostic procedures. These methods require the DNA or RNA sample be free of nuclease as well as all solutions and reagents that come into contact with the sample during processing, as nucleases that degrade either DNA or RNA would compromise the integrity of the results. Nucleic acid amplification reactions such as the polymerase chain reaction (PCR) or ligase chain reaction (LCR) and recombinant DNA cloning techniques are methods that are very sensitive to nuclease degradation. The principle of these and other reactions require very small amounts of target DNA or RNA for detection. However, the increased amplification capabilities of these reactions mean that degraded nucleic acids would be likewise amplified.

The ideal filter element for micro-capillary affinity support in accordance with the present invention should have fixed longitudinal fibers, a loose torturous network, interconnecting chambers, and high thermal resistance, and should be chemically inert until derivatized, biologically inert, and stable over time.

Fiber surface activation can be accomplished in batch or column chromatographic modes, employing conventional procedures. The components needed are those commonly found in basic parts of commercially available low pressure chromatography systems. Elements are loosely packed into standard low pressure glass columns and coupled using such techniques as silylation producing free amino groups that can be later utilized with specific linkers and covalent coupling techniques. One membrane activation strategy employs boiling with nitric acid which produces a free amino group that can be utilized for either homo or heterobifunctional crosslinking, i.e., carbonyldiimadazole, aldehyde, tresyl and tosyl activation . (K. Blau, G. King, Handbook of Derivatives for Chromatography, Heyden and Sons Philadelphia 1977.) A second procedure involves silylation with 3-aminopropyltriethoxysilane, N-(2aminoethyl)-3-aminopropyltrimethoxysilane or N-(6aminohexyl) aminopropyltrimethoxysilane followed by homo or heterobifunctional crosslinking agents such as dialdehyde, sulfosuccinimidyl (4-azidophenylidithio) propionate, m-maleimidobenzyl-N-hydroxysuccinimide ester. (D. Leydon, W. Collins, Silylated Surfaces, Gordon and Breach New York, N.Y. 1980; E. Plueddemann, Silane Coupling Agents, Plenum, New York N.Y. 1982; A. E. Pierce Immunotechnology, Rockford, Ill. 1992; and Weltman J. K., BioTechniques 1 148–152, 1983.)

EXAMPLE 1

The tip 21 and its streptavidin coated porous element 20 are washed with 200 ul binding/washing buffer (1M of NaCl, 5 mM tris, 1 mM EDTA), being certain that all residual fluid is expelled out of the tip 21. The tip and its receptor element 20 are now ready for binding biotinylated DNA. The DNA solution is then mixed with an equal volume of 2× binding/washing buffer. The tip is efficiently loaded from the top with 20–100 ul of DNA buffer mixture. The simplest procedure is slowly to expel and aspirate the ligand fluid five times in a 1.5 ml polypropylene centrifuge tube . Thereafter the tip is washed with three quick 200 ul rinses with washing buffer, and one with distilled water. Strand separation is effected by expelling fluid and adding 20 ul 0.2N NaOH to the top of the tip, thereafter slowly drawing and expelling the solution five times. The tip is then allowed to stand in contact with the solution for at least five minutes. The resulting solution should be saved, since it contains the single strand. Neutralization is then effected by adding 2 ul 1N HCl and 1 ul 1M TRIS, pH 7. The single strand of DNA preparation is now ready to be sequenced, and may be used directly or may be diluted, as required.

To recover the other strand, the same procedures are followed but with the opposite strand biotinylated. Alternatively, cleavable biotin may be used to capture and release both strands, successively.

The above-described example has been effected by using the tip 21 and the one-piece porous receptor 20, as illustrated in FIG. 2. However, in the embodiment shown in FIG. 3, tip 21 contains a modified receptor element 30, which constitutes a multi-layered receptor element. In the embodiment illustrated, element 30 comprises a first layer 31 positioned adjacent the smaller end of the tip 21, a second layer 32 which is seated against the end of layer 31 remote from the small end of the tip, and a third layer 33, which engages layer 32 to sandwich the latter between layers 31 and 33. Each of the layers 31–33, of course, is made from a porous material, such as for example the fibrous material noted above in connection with the receptor element 20. The advantages of using a multilayer receptor 30 include the ability to precoat each layer with a different receptor or ligand, so that they can be utilized for positive and negative controls, or can be used for concurrent measurement of unknowns and controls, thus minimizing assay error, particularly in connection with single measurements. This is particularly handy when the assays are performed in the field. One manner in which the multi-layered element 30 may be utilized is described in the following example.

EXAMPLE 2

Figure 3:
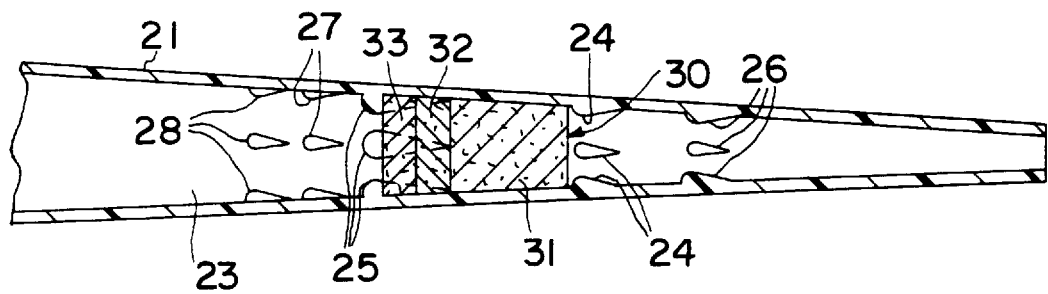
FIG. 3 is an enlarged, fragmentary sectional view similar to FIG. 2, but illustrating a tip made according to a second embodiment of the present invention.

The multilayered reactive element 30 of FIG. 3 can be used for producing self-contained immunoassay controls for measuring Rabbit IgG in serum. For example, goat antibodies raised against rabbit IgG can be covalently immobilized on the reactive element 30 for use in a standard "sandwich" immunoassay. Once bound to this primary antibody, the rabbit IgG is detected by binding to a secondary antibody, chicken anti rabbit IgG, which is coupled to the enzyme alkaline phosphatase (AP). To incorporate controls within the tip 21, and by way of example, layer 31 of element 30 is coupled to goat anti-rabbit IgG, layer 32 is coupled to goat anti-rabbit IgG which has been prebound to rabbit IgG (positive control), and layer 33 is coupled with an inert antibody (negative control). This inert antibody may be any antibody not specifically reacting with the ligand to be measured—i.e., rabbit IgG.

The reactive element 30 is then exposed to a solution of rabbit serum by passing the solution through the tip, thus exposing the reactive layers 31–33 to the sample. Rabbit IgG, if present, will then bind to the middle layer 32. The tip is washed with phosphate buffered saline containing 0.1% Tween (PBS-T) to remove any non-specifically bound proteins. The secondary antibody-AP conjugate properly diluted in PBS is exposed to the reactive element 30 by passing the solution in and out through the tip five times. After another wash in PBS-T, a precipitating chromogenic substrate for AP is passed through the tip and element 30. Where AP is present from the secondary antibody conjugate, the substrate will change color and precipitated at that location. Therefore, the positive control layer 32 will accumulate color, the negative control layer 33 should remain color-free, and the experimental layer 31 will change color proportionally to the amount of IgG bound thereto.

EXAMPLE 3

Purification of polyadenylated mRNA from miniature preparations of total RNA using tip 21 and element 20

The majority of messenger RNA molecules have a tract of poly adenosine (poly A) at their termini. Other types of RNA, ribosomal and transfer RNA, do not. It is a well known procedure for purification of polyadenylated mRNA, that binding to oligo dT-cellulose can be employed to selectively purify these molecules. Purification of mRNA by this method is useful, because subsequent reactions requiring mRNA, such as cDNA cloning or translation of the message to protein in vitro, proceed much more efficiently with high purity mRNA.

Mouse hepatoma cells are grown in standard tissue culture flasks. Cells (105 to 106) are lysed in 1 ml TriReagent (manufacturer). Total RNA is extracted according to standard methods. A biotinylated oligo dT is added to the total RNA in an optimal binding solution: 1M NaCl, 1 mM EDTA, 0.05% SDS at 420° C. for 5 min. The solution is then passed in tip 21 over a reactive element 20 coated with streptavidin. The mRNA now bound to the biotinylated oligo dT is captured in element 30 and is then washed with 1M NaCl, 1 mM EDTA, 0.5% SDS. Purified mRNA is eluted from the tip 21 by exposing the mRNA coated reactive element 20 to 50 microliters of 0.1M NaCl, 1 mM EDTA, 0.5% SDS. The solution containing the purified mRNA may be diluted for immediate use, or the mRNA may be precipitated with 70% ethanol for storage at −20° C.

By associating the biotinylated oligo dT with mRNA in solution, the kinetics of association afforded by porous element 20 are very rapid and efficient. Alternatively, the biotinylated oligo dT may be pre-associated with the streptavidin coated element 20 and processed as a conventional oligo dT chromatography in miniature. Due to the high binding efficiency of the tip 21 and its porous reactive element 20, very small quantities of total RNA are needed to obtain microgram quantities of purified mRNA very rapidly.

EXAMPLE 4

Immobilization of single stranded nucleic acids for self-contained diagnostic assay for mouse actin mRNA using tip 21 and element 20:

Several formats exist for the quantitation of DNA or RNA molecules having a specific sequence of interest. This may be a DNA (or RNA) fragment of the genome of an infectious disease agent, or a DNA (or RNA) sequence of a particular gene from an organism of interest. These techniques rely on the selective and highly specific hybridization between complementary nucleic acid base pairing and have been known to be able to discriminate between single base differences.

The reactive elements 20 or 30 of the current invention may be coated with specific DNA or RNA to be used for diagnostic assays to determine the presence and quantity of a specific nucleic acid. Because of the self contained design of these elements, hybridization is enhanced and stringent washing is accelerated.

Oligonucleotide primers which bracket at 500 base pair fragment of the mouse actin gene are used to amplify mouse actin DNA by standard techniques utilizing polymerase chain reaction. One of the primers is biotinylated and the biotinylated amplified DNA is bound to a streptavidin coated reactive element 20 as in Example No. 1. The non-biotinylated strand of DNA is eluted from the tip with 0.2N NaOH and the tip is washed extensively with distilled water. The element 20 remains coupled to the biotinylated 500 base single strand which is complimentary to the mRNA sequence. It may now be used as an immobilized single stranded DNA to hybridize selectively with samples suspected of containing mouse actin mRNA. The quantity of mRNA is determined by competing with single stranded DNA complementary to the immobilized biotinylated strand bearing another label, such as the enzyme alkaline phosphatase, the fluorescent dye fluorescein, or other appropriate label. The quantity of actin mRNA is then inversely proportional to the measured label.

Alternatively, the labeled complimentary strand may be preassociated with the immobilized biotinylated strand, such that the mRNA displaces the labeled strand proportionally to the concentration of actin mRNA in the sample.

The procedure may be followed with any gene fragment of interest by coating the reactive element with the appropriate single stranded nucleic acid and appropriate labeled strand.

EXAMPLE 5

For the rapid qualitative detection of feline leukemia virus (Felv) in cat serum, a three-layered reactive element test protocol is used. For example, streptavidin activated elements as shown in Example 1 are stacked with both positive and negative control elements to produce a complete test format as follows. The device is washed with buffer solution, sample is drawn into the device and incubated for 4 minutes, and the device is again washed with buffer solution. Antibody conjugate is drawn in, and incubated for 4 minutes, followed by further washing with buffer solution. The cat serum sample is then added to a double anti Felv p27 core protein monoclonal antibody (Mab) mixture having one Mab labeled with biotin and the second Mab which is directed against a separate epitope region, conjugated to the enzyme alkaline phosphatase. The antibody mixture is allowed to react for 3 minutes and the drawn over the triple layer reactive element 30 (FIG. 3) and exposed to said layers for 2 minutes. The sample mixture is expelled and 1 ml TTBS wash buffer is gently expelled through the antibody mixture. Substrate appropriate for precipitating in the presence of alkaline phosphatase is drawn into the tip and covers all three elements. The top element is the positive control and will turn dark if all steps were carried out properly. The second or middle element is the negative control and should remain negative or white with appropriate non specific binding and or washing. The bottom or unknown sample element will turn dark or remain white, depending on a positive or negative result, respectively. A positive result is achieved when the biotin labeled Mab is captured by the streptavidin element and the reporter enzyme labeled secondary Mab is bound to the target if present. Without Felv target epitope there is no binding of secondary reporter Mab.

EXAMPLE 6

Detection of DNase in Tris Buffer Stocks

A 300 base-pair biotinylated target DNA fragment is bound to streptavidin covalently immobilized on the fibrous element. The DNA is also coupled with a reporter molecule, such as alkaline phosphatase. A solution of Tris buffer is drawn into the aligned fiber diagnostic device and incubated 10 minutes at 37° C. If present, DNase in the sample will hydrolyse double stranded DNA and thus release the reporter molecules into the solution. The solution is expelled into alkaline phosphatase chromogenic substrate and is color developed read by visual inspection for a qualitative result, or in a standard spectrophotometer for quantitation. Comparison to known DNase standard dilutions can be made. It is well known that DNase will attack each strand of DNA producing a complex mixture of 5'-phosphate mono and oligonucleotides. The release of reporter molecules accompanies the hydrolysis and it's recognition is unaffected by the process. Depending on such variables as nuclease concentration, specificity i.e., DNAse type, temperature, exposure time, DNase can be measured in a variety of other solutions.

Figure 4:
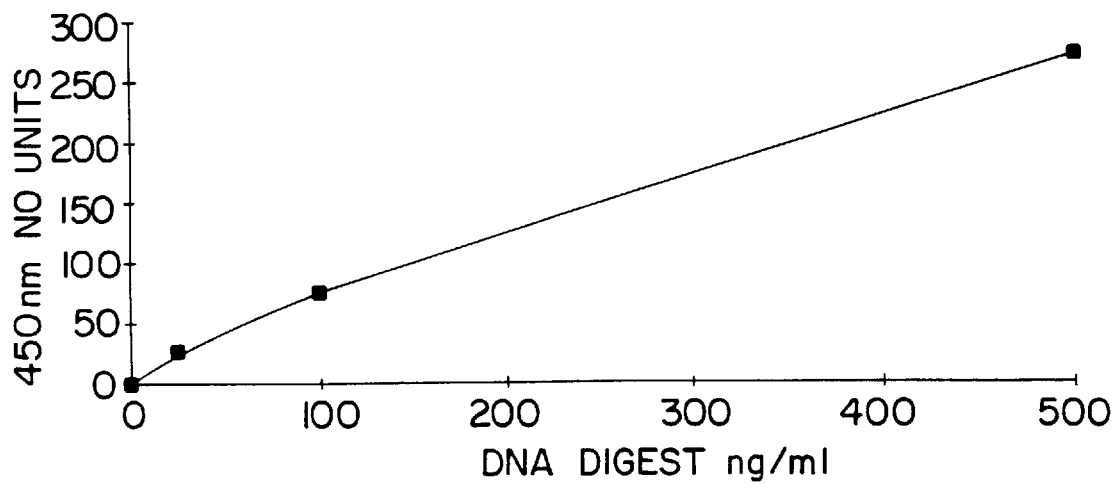
FIG. 4 is a graphical representation of fluorescent DNA detection.
Figure 5:
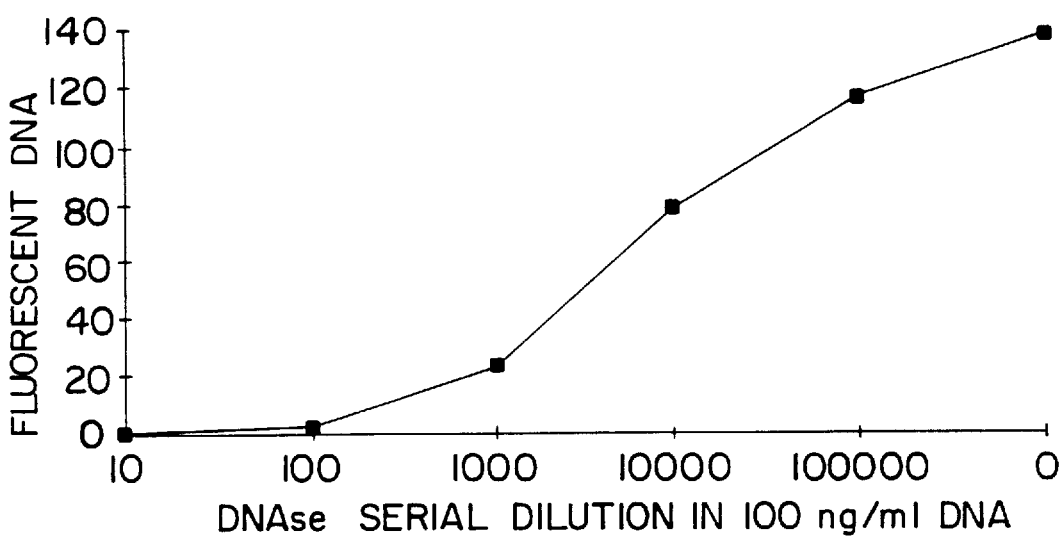
FIG. 5 is a graphical representation of DNase dilution.

Alternatively, if the target DNA fragment is initially constructed with a cleavable biotin, one may measure DNase contamination without a reporter molecule. A solution of Tris buffer is drawn into the aligned fiber diagnostic device and incubated for 10 minutes at 37° C. and the solution is expelled. If present, DNase in the sample will hydrolyse the immobilized target DNA. The cleavable biotin is then exposed to reducing agents that result in cleavage of the biotin label, releasing the immobilized target DNA into solution. The solution is expelled into a test tube containing Hoechst dye 33258 which fluoresces when excited by ultra-violet light. The amount of fluorescence as measured in a standard fluorometer is proportional to the amount of DNA, as seen from FIG. 4. If DNase was in the test solution, some of the immobilized target DNA will be degraded and not available to be measured after release into the Hoechst dye. The amount of DNase contamination will be inversely proportional to the amount of target DNA measured (FIG. 5).

EXAMPLE 7

Detection of Rnase in Cell Lysates

The isolation of intact mRNA is an essential first step in several molecular techniques, such as the preparation of cDNA for subsequent construction of a cDNA library, and measurement of specific mRNA populations. The currently accepted protocol for the detection of RNase in the crude or purified mRNA is to incubate the sample for 30 minutes at 37° C. and electrophorese the sample on a standard 1% agarose gel. Samples are also run for comparison to mRNA aliquots that have been kept frozen and RNA standards. The gel is strained with ethidium bromide. If the RNA is not degraded, sharp bands appear. The appearance of smeared bands, or no bands, indicates the samples contain Rnase. This method is not easy to quantitate and it does not allow for easy testing of solutions to be used in later processing of the RNA.

The present invention may be used to detect RNase by the following method. Target RNA labeled with fluorescein is bound to the fibrous element. Sample suspected of RNase contamination is drawn into the element and incubated at 37° C. for 10 minutes. The solution is expelled and the amount of released fluorescein measured in a fluorometer. If RNase is present, the RNA will be degraded, releasing the fluorescein marker. The amount of fluorescence will be proportional to the amount of RNase contamination in the sample.

EXAMPLE 8

Detection of DNase contamination in fluids completely contained within the Multilayered Fibrous Element One layer of a multilayered fibrous element contains one microgram of a target DNA fragment bound to the fibrous element by covalent attachment of an amino group on one end. The other end is covalently attached to biotinylated alkaline phosphatase (BAP). A second layer is covalently coated with streptavidin. A third layer comprised of blank fibers blocked with gelatin acts as a negative control. A fourth layer comprised of fibers covalently conjugated to alkaline phosphatase acts as a positive control. A 150 microliter sample is exposed to the device for 30 minutes at 37° C. If DNase is in the sample, the enzyme cleaves the target DNA fragment, releasing the BAP. After several passes into and out of the elements, the BAP is captured by the streptavidin layer. After a wash with TTBS, the elements are exposed to alkaline phosphatase precipitating substrate, BCIP/NBT, causing a color development. In the absence of DNase, only the positive control layer and the target DNA-BAP layer develop color. In the presence of DNase, the streptavidin coated second layer also develops color.

From the foregoing it will be apparent that the present invention provides a relatively simple and inexpensive method of improving, among other methods, the method of effecting strand separation for DNA sequencing. This invention also provides an improved activated immunodiagnostic pipette tip containing a receptor element which is capable of capturing substantially greater quantities of the targeted molecules, as compared to prior such devices. For example, by immobilizing a receptor coating on each of the fibers of the fibrous elements 20 and 30 described above, a substantially greater surface area of the receptor material is exposed to a liquid test sample, and consequently the amount of captured molecules can be increased 100 to 1000 fold over the capture rates of the above-described solid support systems. Moreover, the reactive surfaces of the elements 20, 30 may be modified by a number of conventional immobilization chemistries designed to link to proteins, nucleic acids or other specific binding ligands via covalent attachment to a number of reactive chemical groups (i.e., amino, carboxyl, sulfhydryl, etc.) or by non-covalent absorption.

Furthermore, since the interaction between ligand and binding receptor is reversible, molecules bound to an element 20 or 30 may be intentionally eluted and recovered from the tip 21 for further analytical procedures. As an added advantage, several small segments of a reactive element e.g., 31–33 may be stacked, creating the potential for a positive and negative control to be included with an experimental test conducted totally within a single tip 21.

While the porous elements 20, 30 have been described in one form as being made from a fibrous material, it will be apparent that other types of porous structures may be employed, such as honeycombed, porous resin, or membrane type structures which present numerous small surfaces to which a receptor may be immobilized, and which will permit liquid samples and the like to be flushed or aspirated therethrough. When the reactive element, or any portion thereof, is made from a fibrous material such as the above-noted cellulose acetate, activation of the surfaces of the fibers to enable the immobilization of a receptor coating thereon, can be effected by employing any one of several, known procedures.

Moreover, while this application has been illustrated and described in connection with only certain embodiments thereof, it will be apparent that it is capable of still further modification, and that this application is intended to cover any such modifications as may fall within the scope of one skilled in the art, or the appended claims.

What is claimed is:

1. A method of determining whether an analyte capable of binding to a ligand is present in a liquid sample, comprising:
   (a) providing a pipette tip having at least three activated porous bundles of non-biaxially oriented fibrous material therein, said fibrous material comprising a plurality of fibers longitudinally oriented in the direction of sample flow, a first of said at least three porous bundles being a positive control comprising first means covalently coated thereon which indicates the functionality of said first activated porous bundle and of the enzyme introduced in step (c), a second of said at least three activated porous bundles being a negative control for determining whether each of said activated porous bundles blocks the non-specific binding thereto of a secondary ligand or of said analyte, and a third of said at least three activated porous bundles having said ligand covalently coated thereon;
   (b) introducing said liquid sample into said pipette tip, thereby causing any of said analyte present in said liquid sample to contact each of said at least three activated porous bundles;
   (c) introducing into said pipette tip a conjugate ligand coupled to an enzyme, said conjugate ligand being adapted to bind to said first means and to any analyte bound to said ligand bound to said third activated porous bundle; and (d) determining the presence or absence of said analyte in said liquid sample by introducing into said pipette tip a precipitating chromogenic substrate for said enzyme, said chromogenic substrate being adapted to bind to said enzyme and change color upon so binding, thereby generating a signal in said pipette tip.

2. The method of claim 1, wherein said analyte is an antigen and said ligand is an antibody.

3. The method of claim 2, wherein said first means comprises said antigen.

4. The method of claim 3, wherein said positive control further indicates the functionality of said antibody.

5. A pipette tip for determining whether an analyte capable of binding to a ligand is present in a liquid sample, comprising:

at least three activated porous bundles of non-biaxially oriented fibrous material therein, said fibrous material comprising a plurality of fibers longitudinally oriented in the direction of sample flow, a first of said at least three porous bundles being a positive control comprising first means covalently coated thereon which indicates the functionality of said first activated porous bundle and of an enzyme introduced into said pipette tip, a second of said at least three activated porous bundles being a negative control for determining whether each of said activated porous bundles blocks the non-specific binding thereto of a secondary ligand or of said analyte, and a third of said at least three activated porous bundles having said ligand covalently coated thereon.

6. The pipette tip of claim 5, wherein said analyte is an antigen and said ligand is an antibody.

7. The pipette tip of claim 6, wherein said first means comprises said antigen.

8. The pipette tip of claim 7, wherein said positive control further indicates the functionality of said antibody.

* * * * *